United States Patent
Knappen et al.

(10) Patent No.: US 7,145,076 B2
(45) Date of Patent: Dec. 5, 2006

(54) METHOD FOR MINIMIZING STRESS IN FEEDTHROUGH CAPACITOR FILTER ASSEMBLIES

(75) Inventors: Scott Knappen, Annapolis, MD (US); Robert Naugler, Eldersburg, MD (US); Haytham Hussein, Woodstock, MD (US); Thomas Shipman, Frisco, MD (US); Richard Brendel, Carson City, NV (US); Christine Frysz, Marriottsville, MD (US)

(73) Assignee: Greatbatch, Inc., Clarence, NY (US)

( * ) Notice: Subject to any disclaimer, the term of this patent is extended or adjusted under 35 U.S.C. 154(b) by 0 days.

(21) Appl. No.: 11/307,434

(22) Filed: Feb. 7, 2006

(65) Prior Publication Data

US 2006/0175071 A1    Aug. 10, 2006

Related U.S. Application Data

(60) Provisional application No. 60/651,052, filed on Feb. 8, 2005.

(51) Int. Cl.
*H01J 5/00*    (2006.01)

(52) U.S. Cl. .................. 174/50.6; 174/50.6; 174/50.56; 174/50.61; 361/302; 29/25.42

(58) Field of Classification Search ............... 174/50.6, 174/50.56, 50.61, 50.63; 361/302, 303, 307; 29/25.42
See application file for complete search history.

(56) References Cited

U.S. PATENT DOCUMENTS

| 4,217,137 A | * | 8/1980 | Kraska et al. ............... 420/507 |
|---|---|---|---|
| 4,792,503 A | | 12/1988 | Eppley |
| 5,033,666 A | | 7/1991 | Keusseyan et al. |
| 5,333,095 A | * | 7/1994 | Stevenson et al. .......... 361/302 |
| 6,131,796 A | | 10/2000 | Kaja et al. |
| 6,180,909 B1 | | 1/2001 | Quick et al. |
| 6,335,117 B1 | | 1/2002 | Yoshida et al. |
| 6,554,178 B1 | | 4/2003 | Tsukamoto |
| 6,696,199 B1 | | 2/2004 | Yoshida et al. |
| 6,716,554 B1 | | 4/2004 | Tsukamoto et al. |
| 6,841,731 B1 | * | 1/2005 | Zanello ................... 174/50.56 |
| 6,852,925 B1 | * | 2/2005 | Wolf et al. ................ 174/50.6 |
| 2003/0091897 A1 | | 5/2003 | Oogaku et al. |
| 2004/0101746 A1 | | 5/2004 | Ota et al. |

* cited by examiner

*Primary Examiner*—Dhiru R. Patel
(74) *Attorney, Agent, or Firm*—Michael F. Scalise

(57) ABSTRACT

A feedthrough terminal pin assembly includes an outer ferrule hermetically sealed through a braze joint to an insulator seated within the ferrule is described. The insulator is also hermetically brazed to at least one terminal pin. The terminal pin is provided with a braze retention structure such as an annular groove that prevents braze material from filleting past the groove. Similarly, either the ferrule or the insulator is provided with a retention structure such as an annular groove that prevents braze material spill out from the insulator/ferrule interface. In that manner, the braze retention structures keep braze material from accumulating in unwanted areas where it could adversely affect hermeticity as well as proper attachment of an EMI filter to the feedthrough assembly.

14 Claims, 8 Drawing Sheets

METHOD FOR MINIMIZING STRESS IN FEEDTHROUGH CAPACITOR FILTER ASSEMBLIES

BACKGROUND OF THE INVENTION

1. Field of the Invention

This invention relates generally to a hermetic feedthrough terminal pin assembly, preferably of the type incorporating a capacitor filter. More specifically, this invention relates to feedthrough terminal pin capacitor filter assemblies, particularly of the type used in implantable medical devices such as cardiac pacemakers, cardioverter defibrillators, and the like, to decouple and shield internal electronic components of the medical device from undesirable electromagnetic interference (EMI) signals. The feedthrough assembly provides a hermetic seal that prevents passage or leakage of fluids into the medical device.

2. Prior Art

Feedthrough terminal pin assemblies are generally well known in the art for use in connecting electrical signals through the housing or case of an electronic instrument. For example, in an implantable medical device such as a cardiac pacemaker, a defibrillator, and the like, the feedthrough assembly comprises one or more conductive terminal pins supported by an insulator structure seated in the ferrule. Suitable materials may for the ferrule include titanium, tantalum, niobium, stainless steel or combinations of alloys thereof. The ferrule may be of any geometry including round, rectangle, and oblong.

The terminal pins are typically composed of platinum or a combination of platinum and iridium and provide for passage of electrical signals from the exterior to the interior of the medical device. Platinum and platinum-iridium alloys are biocompatible materials that create a hermetic seal through a gold brazing process that seals any gap between the terminal pin and the supporting insulator. A gold brazing process is also used to hermetically seal any gap between the supporting ferrule and the insulator.

However, too much braze material at the insulator/ferrule interface or at the insulator/terminal pin interface can cause excess tensile stresses leading to cracking of the ceramic insulator with possible subsequent loss of hermeticity. Another problem with hermetic seals at the feedthrough interfaces occurs if the space allotted for the braze material is insufficient to hold or receive its volume. In that case, the braze material can spill out of its interface channel. In addition to causing a weak braze joint and potentially compromising hermeticity, braze spill out presents an esthetic condition that adversely impacts scrap. Also, if an EMI filter is subsequently attached to the feedthrough to attenuate unwanted EMI interference, a flat attachment surface, free of braze spill out, is needed.

Other problems related to excessive braze material at the feedthrough interfaces include unwanted wetting of critical areas. One place this occurs is at the feedthrough perimeter where the ferrule is laser welded to the device shield. Excessive braze material at this interface can compromise the hermetic seal between the ferrule and the device shield.

A second area of concern is on the surface of the insulator between the terminal pins. Over wetting in this area can result in excessive braze material between two terminal pins. This can shorten the pin-to-pin distance which, under high voltage conditions, can cause arcing, or in the case of a filtered feedthrough, premature dielectric breakdown. Another problem is that excessive flow of braze material on the insulator surface can sporadically dewet, then solidify leaving behind small braze balls on the insulator. This unwanted material can also cause arcing or dielectric breakdown under high voltage conditions.

Wetting of the terminal pin below the insulator/terminal pin interface creates another potential problem area. The flex circuit or wire bond substrate leading to the device control circuitry is subsequently welded to the terminal pin here and electrical shorting can occur should the flex circuit come into contact with this excess braze material.

FIGS. 1 and 2 show a feedthrough 10 compromised by excess braze to further illustrate some of these problems. The feedthrough terminal pin assembly 10 comprises a so-called unipolar configuration having a terminal pin 12 extending through a bore in an electrically insulating or dielectric material such as an alumina or fused glass type or ceramic-based insulator 14, hereinafter collectively referred to as an insulator, nested within a ferrule 16. A layer of metal may be applied to the surface of the insulating material, referred to as metallization, to aid in the creation of a brazed hermetic seal. Metallization materials include titanium, niobium, tantalum, gold, molybdenum, silver, platinum, copper, or combinations thereof. The metallization layer may be applied by various processes including sputtering, e-beam deposition, jet vapor deposition, pulsed laser deposition, chemical vapor deposition, plating, electro-less plating or cladding.

The ferrule 16 comprises a cylindrically-shaped body 18 having an upper annular flange 20 extending outwardly along a plane generally perpendicular to the longitudinal axis of the ferrule body. The ferrule body 18 comprises a cylindrically-shaped outer wall sized to snuggly fit in an opening 22 provided in the device shield 24 with the flange 20 resting on an outer surface thereof.

The ferrule body 18 also has a cylindrically-shaped inner wall extending to a lower inwardly-extending annular lip 26 that is sized to receive the insulator 14 in a snug-fitting relationship. That way, the lower end surface 28 of the insulator 14 is coplanar with the lower end surface 30 of the ferrule body. With the insulator 14 seated in the ferrule 16 in this manner, an annulus 32 is formed between them extending along the length of the cylindrically-shaped inner wall of the ferrule body 18 from the annular lip 26 to an annular cut-out channel 34 where the flange 20 meets the body.

A ring-shaped braze pre-form (not shown) is received in the cut-out. Non-liming examples of braze material include gold, particularly gold alloys, and silver. Heating the preform causes it to melt and flow into the annulus 32 between the insulator 14 and the ferrule body 18. Upon cooling, the resulting braze 36 now hermetically seals the insulator 14 to the ferrule 16 along the entire length of the annulus 32 and the cut-out 34. However, too much braze material was used and some has spilled out of the cut-out 34, collecting on the upper surface of the ferrule 16. This is shown as braze spill out 36A in FIG. 2.

The insulator further comprises a bore 38 that is sized to provide an annulus 40 between it and the terminal pin 12. A frusto-conically shaped cut-out 42 is provided in the upper surface 44 of the insulator in communication with the annulus 40. A ring-shaped braze pre-form (not shown) is received in this cut-out 42. As with the previously described ferrule braze pre-form, heating the terminal pin pre-form causes it to melt and flow into the annulus 40 between the insulator 14 and the terminal pin 12. Upon cooling, the resulting braze 46 hermetically seals the terminal pin 12 to the insulator 14 along the entire length of the annulus 40. However, too much braze material was used and some has filleted part way up the terminal pin past the upper surface 44 of the insulator 14. This filleting is caused by the difference in the coefficients of friction of the braze material 46 and the terminal pin 12. Braze filleting is undesirable for a number of reasons. Foremost is that it can impair proper attachment of an EMI filter or a molded header assembly to the terminal pin 12 at the upper surface of the insulator. Excess braze material on the terminal pin is also aesthetically unacceptable.

A weld 48 hermetically seals the flange perimeter to the shield 24.

Therefore, there is a need for feedthrough structures that prevent filleting and spill out of braze materials into areas where they can compromise hermeticity as well as prevent the proper attachment of EMI filters and header assemblies to the medical device at the feedthrough. The present feedthroughs provide just such structures.

SUMMARY OF THE INVENTION

In a preferred form, the feedthrough terminal pin assembly comprises an outer ferrule hermetically sealed through a braze joint to an insulator seated within the ferrule. The insulator is also hermetically brazed to at least one terminal pin. That way, the feedthrough assembly prevents leakage of fluid, such as patient body fluid in a human implant application, past the hermetic seal at the insulator/ferrule interface and at the insulator/terminal pin interface.

A filter capacitor having first and second sets of conductive electrode plates embedded within an insulative or dielectric body such as a monolithic ceramic body is mounted to the ferrule. One set of the conduction plates is electrically connected to the terminal pin while the other set is electrically connected to the grounded ferrule. The filter capacitor prevents unwanted EMI signals from transmitting via the terminal pins into the interior of the medical device. In order for the filter capacitor to function, it must be properly seated on the ferrule and possibly the insulator. Braze material filleted onto the terminal pin and braze spill out can hinder EMI filter attachment.

However, according to the present invention, the terminal pin is provided with a braze retention structure such as an annular groove that prevents braze material from filleting past the groove. Similarly, either the ferrule or the insulator is provided with a retention structure such as an annular groove that prevents braze material spill out from the insulator/ferrule interface. In that manner, the braze retention structures keep braze material from accumulating in unwanted areas where it could adversely affect hermeticity as well as proper attachment of the EMI filter to the feedthrough assembly.

These and other objects and advantages of the present invention will become increasingly more apparent by a reading of the following description in conjunction with the appended drawings.

DETAILED DESCRIPTION OF THE PREFERRED EMBODIMENTS

Figure 3:
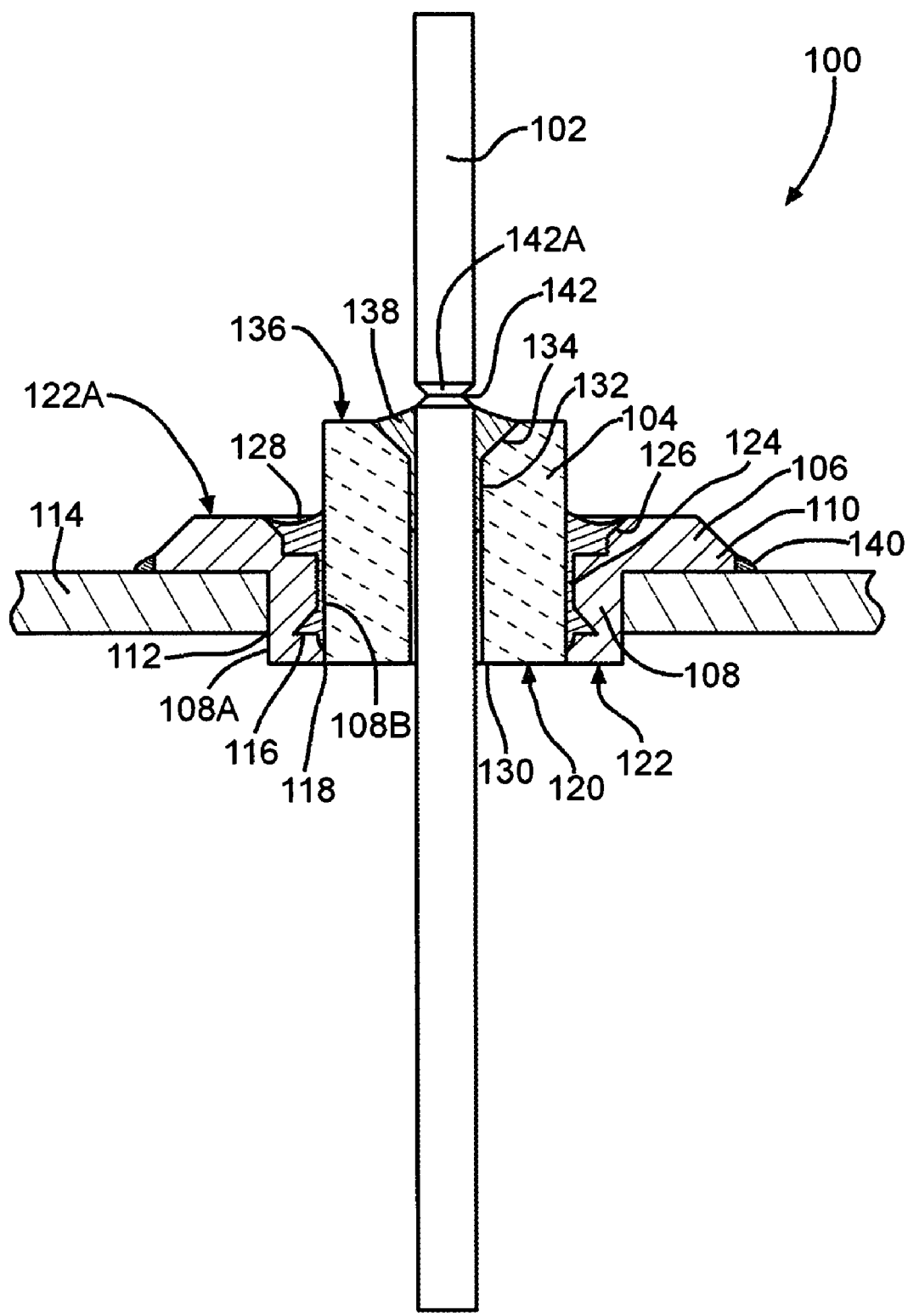
FIG. 3 is a side elevation view, partly in cross-section, showing a feedthrough assembly 100 comprising a ferrule 106 with an internal annular channel 116 and a notched terminal pin 102 for receiving excess braze materials according to the present invention.

FIG. 3 illustrates a feedthrough assembly 100 according to the present invention. The feedthrough assembly 100 is used in a cardiac pacemaker or defibrillator, and the like, for hermetically sealing the interior of the medical instrument against ingress of patient body fluids which could otherwise disrupt instrument operation or cause instrument malfunction. The unipolar feedthrough assembly 100 is similar in structure to the previously described prior art feedthrough assembly 10 except for a unique ferrule structure and terminal pin structure.

The feedthrough 100 comprises a terminal pin 102 extending through a bore in an insulator 104 seated within a ferrule 106. The ferrule 106 comprises an annular-shaped body 108 having an upper annular flange 110 extending outwardly along a plane generally perpendicular to the longitudinal axis of the ferrule body. The ferrule body 108 comprises a cylindrically-shaped outer sidewall 108A that fits snuggly in an opening 112 provided in the device shield 114 with the flange 110 resting on an outer surface thereof.

Unique to the present invention is a braze retention structure in the form of a sideways facing V-shaped annular groove 116 extending from the inner ferrule sidewall 108B part way through the sidewall thickness. The V-shaped groove 116 is located adjacent to a lower inwardly-extending annular lip 118 that is sized to receive the insulator 104 in a snug-fitting relationship with the lower insulator surface 120 being coplanar with the lower ferrule surface 122. With the insulator 104 properly seated in the ferrule 106, an annulus 124 is formed between them extending along the length of the inner wall 108B of the ferrule body 108 from the annular lip 118 to an annular cut-out channel 126 where the flange 110 meets the body 108. The annular cut-out 126 comprises a squared-off lower portion transitioning into a chamfered upper portion. Of course, the cut-out 126 could be completely squared-off or completely chamfered.

During the brazing process, a ring-shaped braze pre-form (not shown) is received in the annular cut-out 126. When heated this, pre-form melts and flows into the annulus 124 between the insulator 104 and the ferrule body 108. Upon cooling, the resulting braze 128 hermetically seals the insulator 104 to the ferrule 106 along the entire length of the annulus 124 and the cut-out 126. However, the V-shaped groove 116 has taken up some of the braze, which is retained therein. Since there was no retaining structure in the prior art feedthrough 10, the excess braze material had created braze spilled out 36A on the upper surface 44 of the ferrule flange 20.

An important aspect of the present invention is that the annular groove 116 is a braze retention structure while the annular cut-out 126 is not. The distinction is that the groove 116 is an annular recess positioned at a location between the lower ferrule end surface 122 and an upper ferrule end surface 122A without being in direct fluid flow communication with either end surface 122, 122A. In contrast, the annular cut-out 126 is in direct fluid flow communication with the upper ferrule end surface 122A.

The insulator 104 further comprises a bore 130 that provides an annulus 132 between it and the terminal pin 102. A frusto-conically shaped annular cut-out 134 is provided in the upper surface 136 of the insulator in communication with the annulus 132. A ring-shaped braze pre-form (not shown) is received in the cut-out 134. When heated, this pre-form melts and flows into the annulus 132 between the insulator 104 and the terminal pin 102. Upon cooling, the resulting braze 138 hermetically seals the terminal pin 102 to the insulator 104 along the entire length of the annulus 132. A weld 140 hermetically seals the flange perimeter to the shield 114.

In a similar manner as the V-shaped groove 116 provided in the ferrule sidewall, the terminal pin 102 is provided with an annular groove 142 extending part way into its diameter. The groove 142 is positioned along the length of the terminal pin 102 so that the braze material partially fills into the groove, but is prevented from filleting past it. This is because the difference in the coefficients of the friction of the braze material and the terminal pin material is not great enough to permit braze from moving along and past the overhang portion 142A of the groove. In that light, the groove 142 is positioned along the length of the terminal pin 102 at a location that is the maximum height to which it is desired to have the braze material contacting the pin.

Figure 4A:
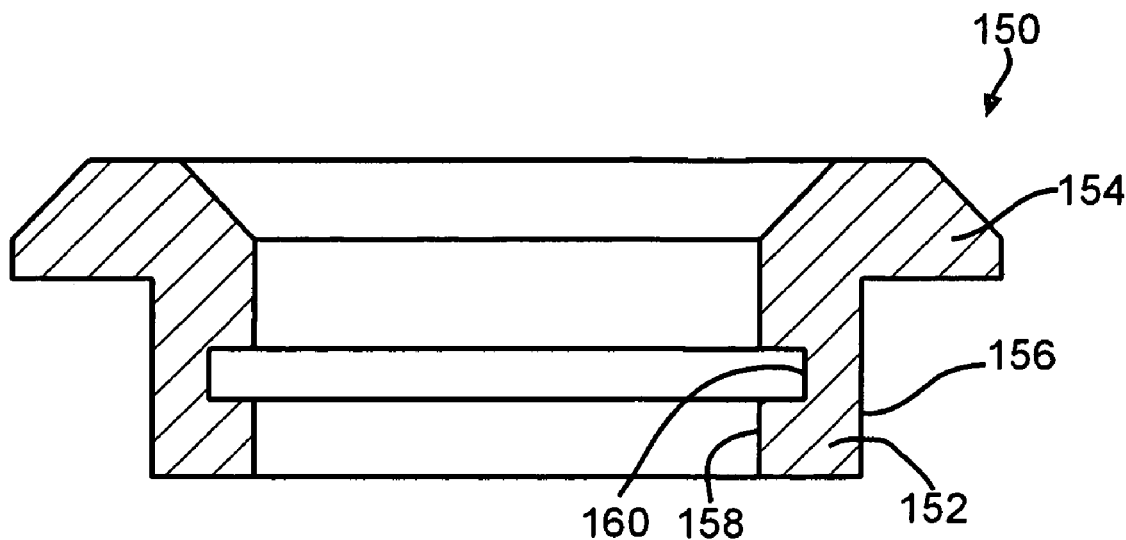
FIGS. 4A and 4B are cross-sectional views of alternate embodiments of ferrules comprising an internal annular channel for receiving excess braze according to the present invention.
Figure 4B:
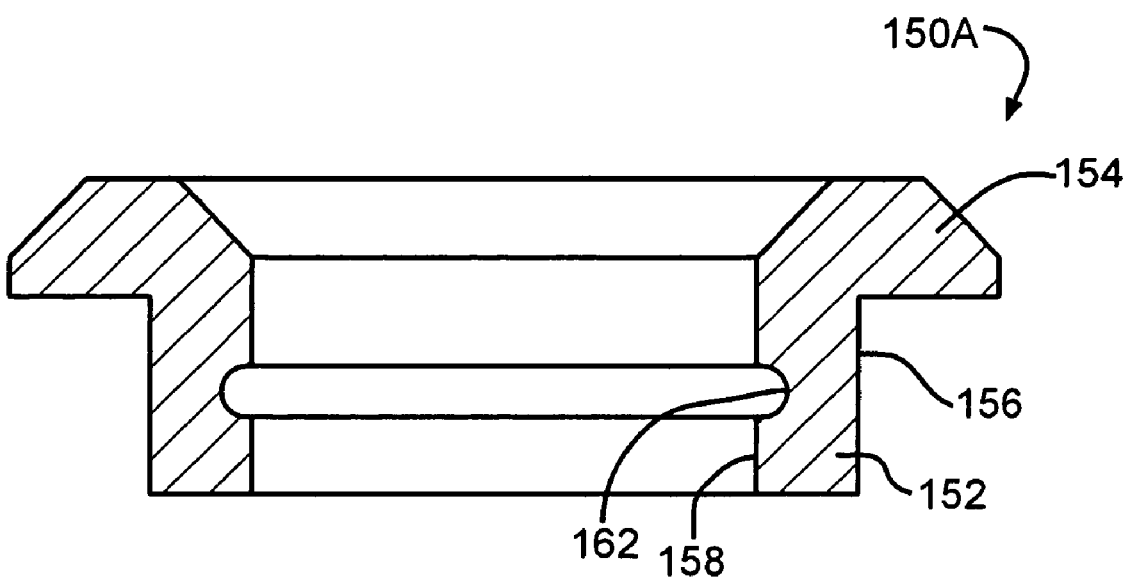

FIGS. 4A and 4B illustrate alternate embodiments of ferrules according to the present invention. FIG. 4A shows a ferrule 150 comprising an annular-shaped body 152 having an upper annular flange 154. The ferrule body 152 comprises a cylindrically-shaped outer sidewall 156 and an inner sidewall 158. In this embodiment, a braze retention structure in the form of an annular channel 160 having generally squared off sides extends from the inner sidewall 158 part way through the sidewall thickness. In all other respects, this ferrule 150 is similar to the ferrule 106 described in FIG. 3.

FIG. 4B shows another embodiment of a ferrule 150A similar to that shown in FIG. 4A except its braze retention structure is in the form of a sideways facing U-shaped or radiused-shaped channel 162 extending from the inner sidewall 158 partway through the sidewall thickness. In each embodiment, it can be seen that the channels 160, 162 do not communicate with either the upper or lower end surfaces of their respective ferrules 150, 150A.

Figure 5:
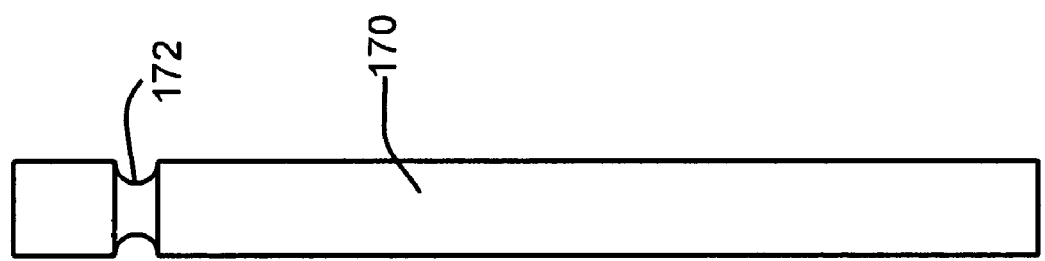
FIG. 5 is a side elevational view of an alternate embodiment of a terminal pin 170 comprising an annular channel 172 for receiving excess braze according to the present invention.

FIG. 5 shows an alternate embodiment of a terminal pin 170 that is useful with the feedthrough 100 of FIG. 3. Terminal pin 170 is similar to terminal pin 102 except the annular groove 172 serving as the braze retention structure has a sideways facing U-shape or radiused-shape.

Figure 6:
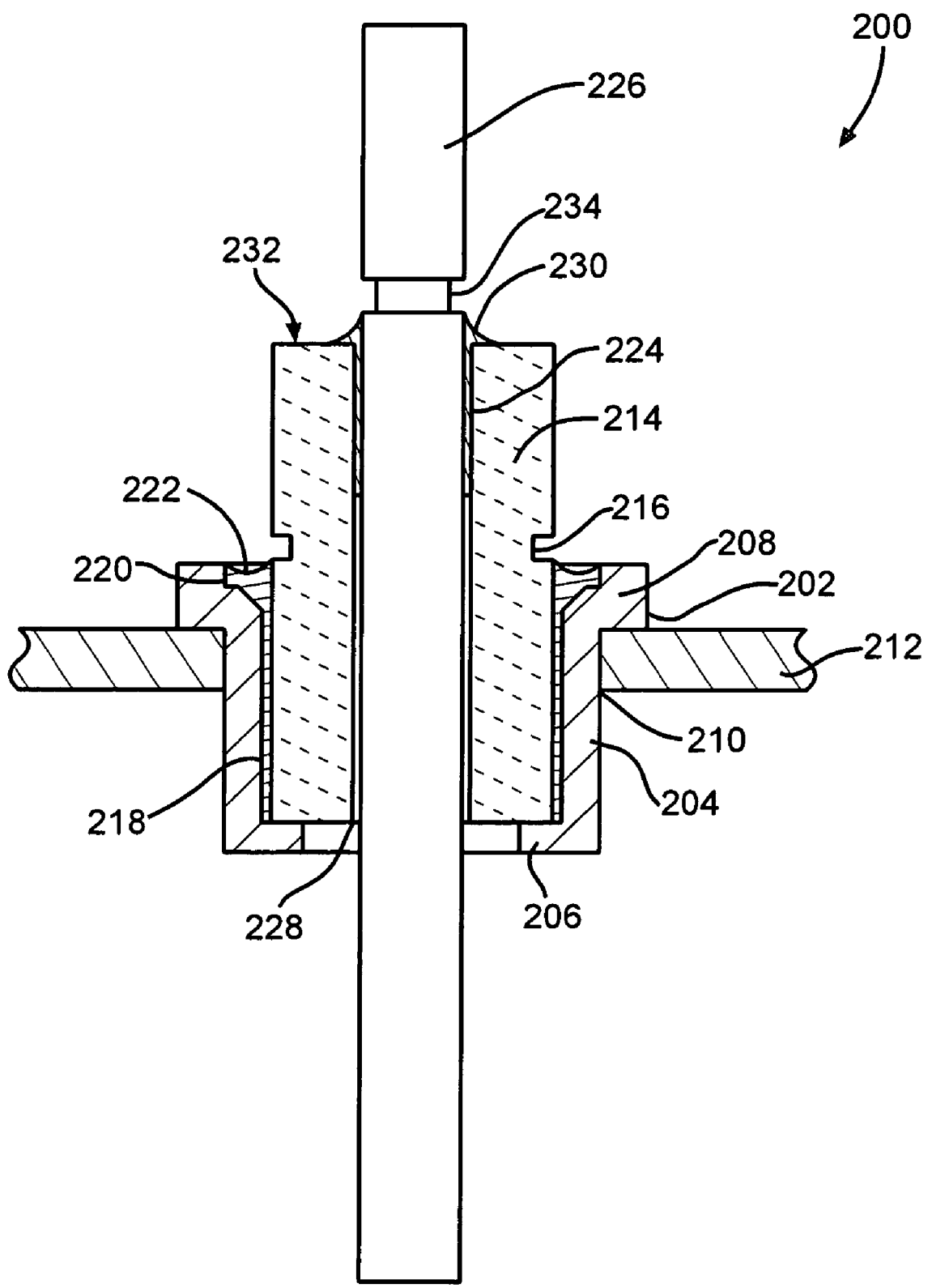
FIG. 6 is a side elevational view, partly in cross-section, of an alternate embodiment of a feedthrough assembly 200 comprising an insulator 214 with an annular groove 216 and a terminal pin 226 with an annular groove 232, both for receiving excess braze according to the present invention.

FIG. 6 illustrates another embodiment of a feedthrough 200 according to the present invention. The feedthrough 200 comprises a ferrule 202 having a cylindrically-shaped body 204 meeting an inwardly extending annular flange 206 at its lower end and an outwardly extending annular flange 208 at its upper end. The ferrule body 204 is received in an opening 210 in the device shield 212 in a snug-fitting relationship with the flange 208 resting on the outer surface thereof.

The insulator 214 is a cylindrically-shaped member that is received in the ferrule 202, resting on the inner flange 206. The insulator 214 is provided with a braze retention structure in the form of an annular channel 216 located between the opposed insulator ends without being in direct fluid flow communication with either of them. The annular channel 216 has a generally squared off sides extending part way into the thickness of the insulator.

Figure 1:
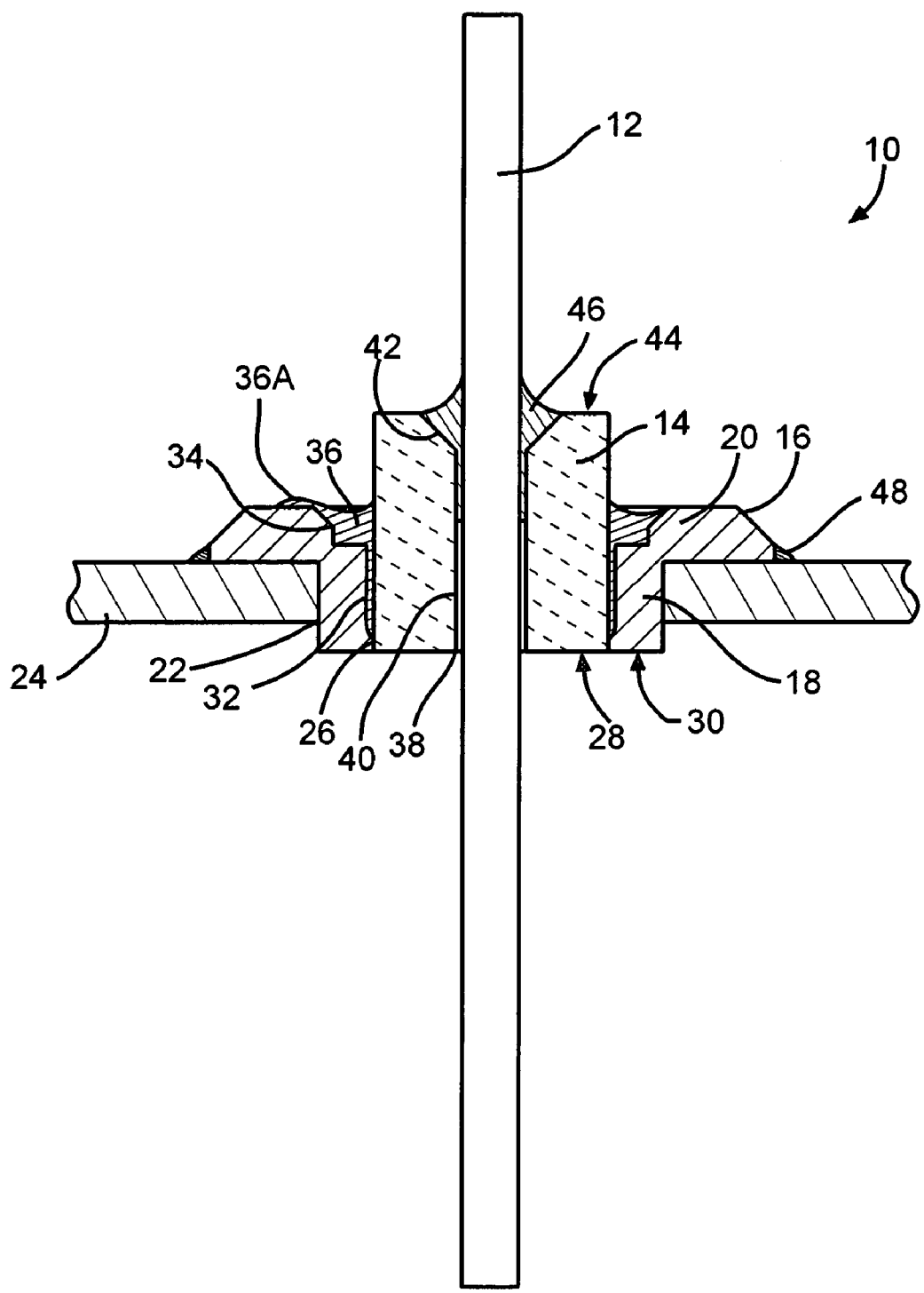
FIG. 1 is a side elevational view, partly in cross-section, of a prior art unipolar feedthrough assembly.
Figure 2:
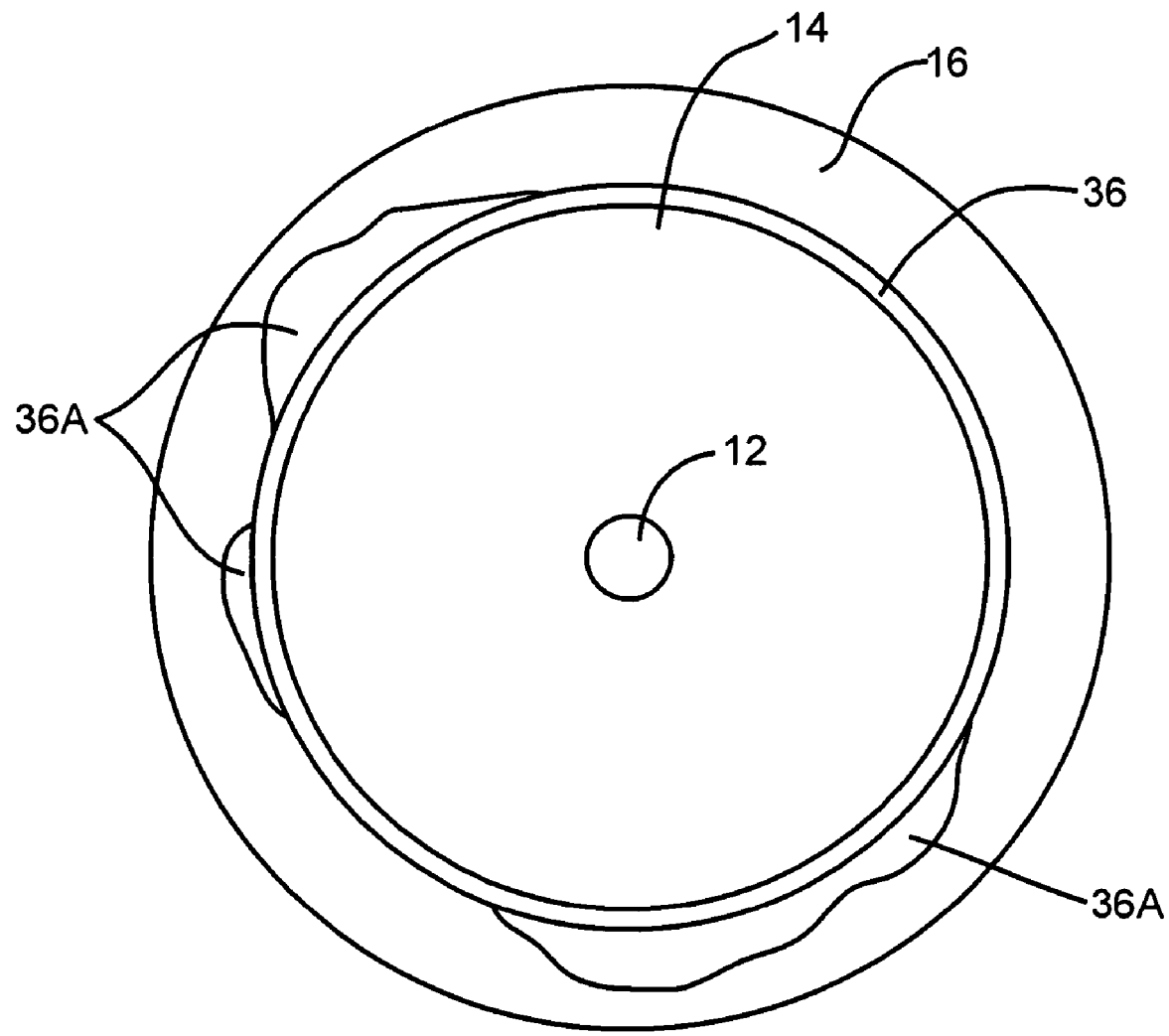
FIG. 2 is a plan view of the prior art feedthrough assembly shown in FIG. 1.

An annulus 218 between the ferrule body 204 and the insulator 214 extends to an annular cut-out 220 where the outer flange 208 meets the body 204. A ring-shaped braze pre-form (not shown) is received in the cut-out. When heated, this pre-form melts and flows into the annulus 218 between the insulator 214 and ferrule body 204. Upon cooling, braze material 222 hermetically seals between the insulator 214 and the ferrule 202 along the annulus 218 and cut-out 220. However, the annular channel 216 has taken up some braze material, which is retained therein. Since there was no retaining structure in the prior art feedthrough 10 (FIGS. 1 and 2), the excess braze material had created braze spill out 36A on the upper surface 44 of the ferrule flange 20.

A second braze pre-form (not shown) is positioned at the annulus 224 between the insulator 214 and a terminal pin 226 received in a bore 228 extending along the length of the insulator. Upon heating, braze material flows down the annulus 224 to create a hermetic seal there. However, some braze material 230 creeps up the terminal pin 226 above the upper surface 232 of the insulator. In a similar manner as the groove 216 provided in the insulator 214, the terminal pin 226 is provided with a braze retention structure in the form of an annular groove 234 extending part way into its diameter. The groove 234 is positioned along the length of the terminal pin 226 so that the braze material partially fills into the groove, but is prevented from filleting past it. In that light, the groove 234 is positioned along the length of the terminal pin 226 at a location that is the maximum height to which it is desired to have the braze material contacting the pin.

Figure 7A:
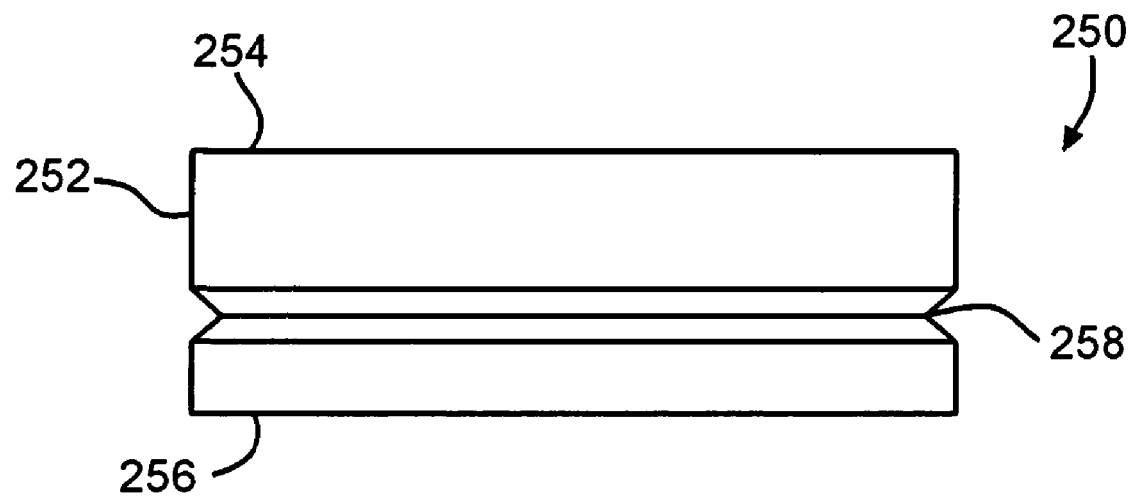
FIGS. 7A and 7B are side elevational views of alternate embodiments of insulators having an annular groove for receiving excess braze material according to the present invention.
Figure 7B:
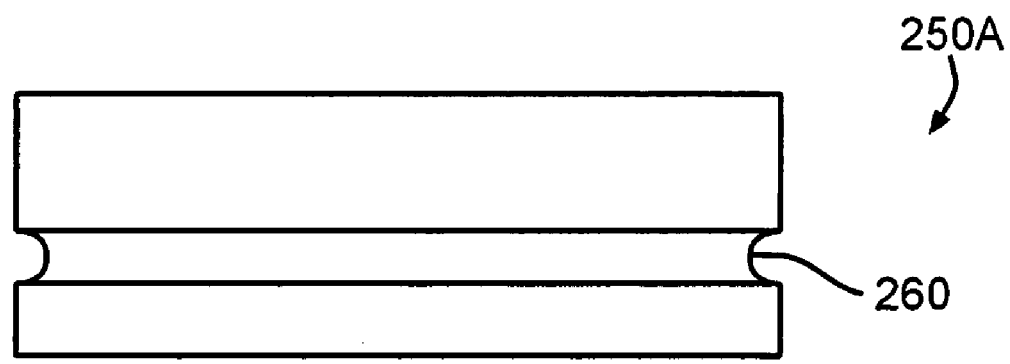

FIGS. 7A and 7B illustrate alternate embodiments of insulators according to the present invention. FIG. 7A shows an insulator 250 comprising a cylindrical sidewall 252 extending between upper and lower or first and second end surfaces 254, 256. A braze retention structure in the form of a sideways facing V-shaped groove 258 is provided in the sidewall 252 without being in direct fluid flow communication with either end. It serves the same function as the groove 216 shown with insulator 214 in FIG. 6. Similarly, FIG. 7B illustrates an insulator 250A similar to that shown in FIG. 7A except the groove 260 has a sideways facing U- or radiused-shape.

Figure 8:
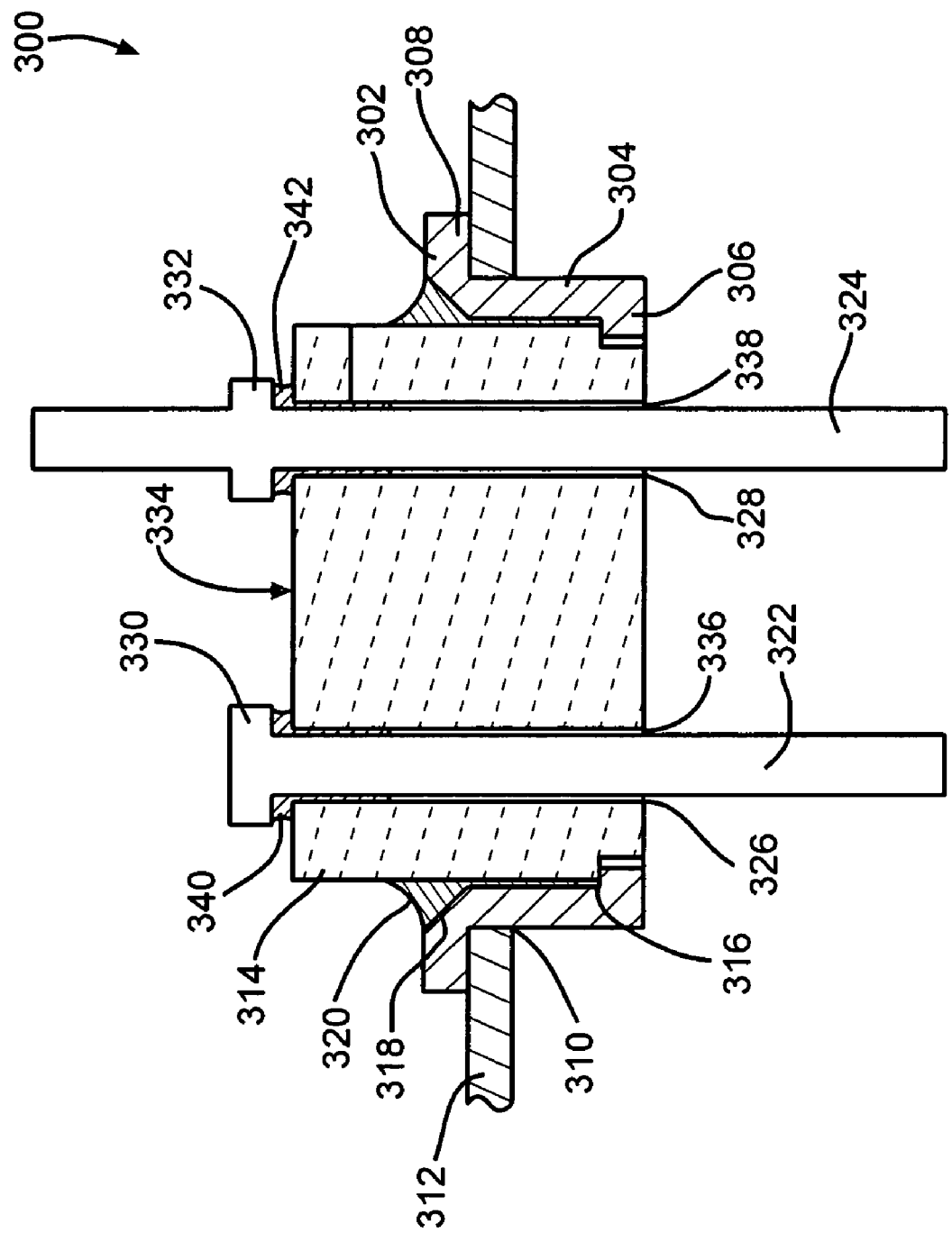
FIG. 8 is a side elevational view, partly in cross-section of another embodiment of a feedthrough assembly according to the present invention.

FIG. 8 illustrates another embodiment of a feedthrough 300 according to the present invention. The feedthrough 300 comprises a ferrule 302 having a cylindrically-shaped body 304 meeting an inwardly extending annular flange 306 at its lower end and an outwardly extending annular flange 308 at its upper end. The ferrule body 304 is received in an opening 310 in the device shield 312 with the flange 308 resting on the outer surface thereof.

The insulator 314 is received in the ferrule 302, resting on the inner flange 306. An annulus 316 between the ferrule body 304 and the insulator 314 extends to an annular cut-out 318 where the outer flange 308 meets the body 304. A ring-shaped braze pre-form (not shown) is received in the cut-out. When heated, this pre-form melts and flows into the annulus 316 between the insulator 314 and ferrule body 304.

Upon cooling, braze material 320 hermetically seals between the insulator 314 and the ferrule 302 along the annulus 316 and cut-out 318.

Terminal pins 322 and 324 are received in respective a bores 326 and 328 extending along the length of the insulator. Terminal pin 322 is a cylindrically-shaped member having a head 330 at one end while terminal pin 324 has its head at an intermediate location between its ends. In both pins, the heads 330, 332 are positioned spaced above an upper end surface 334 of the insulator 314. Braze pre-forms (not shown) are positioned at the annulus 336 between the insulator 314 and the terminal pin 322 and at an annulus 338 between the insulator and the terminal pin 324. Upon heating, braze material flows down the annuluses 336, 338 to create hermetic seals there. However, some braze material 340, 342 creeps up the terminal pins 322, 324 above the upper surface 334 of the insulator. The head 330 on terminal pin 322 acts as a braze retention structure that prevents braze material from filleting past it. Similarly, the head 332 on terminal pin 324 acts as a braze retention structure. This is because the differences in the coefficients of friction between the braze material and that of the terminal pins is not so great as to enable braze material to flow past the respective heads 330, 332. Instead, the braze material is captured under the terminal pin heads. Restricting the location of the braze material to directly under the heads helps reduce stress exerted at the edge of the bores 326, 328 at the upper insulator end surface 334 by the braze.

Thus, various embodiments of braze retention structures have been shown and described. In some of the embodiments, the braze retainer comprises an annular groove-type structure that is positioned between the opposed ends of a terminal pin, ferrule or insulator and in direct braze flow communication with an annulus there between. In other embodiments, the braze retention structure comprises a headed terminal pin that confines the braze to a relatively small gap between it and the insulator end surface. In either case, the retaining structures takes up excess braze material that might flow or wet onto surfaces where it is not needed to affect a hermetic seal. Instead, this unwanted braze material can cause a myriad of problems as discussed in the prior art section. The present braze retention structures prevent such problems from occurring.

It is appreciated that various modifications to the invention concepts described herein may be apparent to those of ordinary skill in the art without departing from the scope of the present invention as defined by the appended claims.

What is claimed is:

1. A feedthrough, which comprises:
  a) an insulator of electrically non-conductive material having a height defined by an insulator sidewall extending to a first insulator end and a second insulator end, wherein the insulator has at least one terminal pin bore extending from the first end to the second end thereof;
  b) a terminal pin received in the terminal pin bore, the terminal pin having a sidewall extending to opposed first and second ends disposed spaced from the respective first and second insulator ends;
  c) a ferrule of an electrically conductive material and comprising a ferrule opening defined by a surrounding sidewall extending to a first ferrule end and a second ferrule end, wherein the insulator is supported in the ferrule opening;
  d) a first braze material hermetically sealing the terminal pin to the insulator and a second braze material hermetically sealing the insulator to the ferrule; and
  e) wherein the feedthrough comprises at least one braze retaining structure selected from the group consisting of:
    i) a first annular groove provided in the terminal pin sidewall at an intermediate location between the first and second terminal pin ends;
    ii) a second annular groove provided in the insulator sidewall at an intermediate location between the first and second insulator ends; and
    iii) a third annular groove provided in the ferrule sidewall at an intermediate location between the first and second ferrule ends.

2. The feedthrough of claim 1 wherein the insulator includes a bevel where the first braze seals between the terminal pin and the insulator and wherein the ferrule includes a bevel where the second braze seals between the ferrule and the insulator.

3. The feedthrough of claim 1 wherein the the first terminal pin end is spaced above the first insulator end.

4. The feedthrough of claim 1 wherein the first insulator side is spaced above the first ferrule end.

5. The feedthrough of claim 1 wherein the first annular groove provided in the terminal pin sidewall, the second annular groove provided in the insulator sidewall, and the third annular groove provided in the ferrule sidewall are each selected from an annular channel, a sideways facing V-shaped channel and a radiused channel.

6. A feedthrough, which comprises:
  a) an insulator of electrically non-conductive material having a height defined by an insulator sidewall extending to a first insulator end and a second insulator end, wherein the insulator has at least one terminal pin bore extending from the first end to the second end thereof;
  b) a terminal pin received in the terminal pin bore, the terminal pin having a sidewall extending to opposed first and second ends disposed spaced from the respective first and second insulator ends;
  c) a ferrule of an electrically conductive material and comprising a ferrule opening defined by a surrounding sidewall extending to a first ferrule end and a second ferrule end, wherein the insulator is supported in the ferrule opening;
  d) a first braze material hermetically sealing the terminal pin to the insulator and a second braze material hermetically sealing the insulator to the ferrule;
  e) wherein the terminal pin comprises a first annular groove as a first braze retaining structure provided in the terminal pin sidewall at an intermediate location between the first and second terminal pin ends; and
  f) wherein at least one of the insulator and the ferrule comprise a second braze retaining structure selected from the group consisting of:
    i) the insulator comprises a second annular groove provided in the insulator sidewall at an intermediate location between the first and second insulator ends; and
    ii) a third annular groove provided in the ferrule sidewall at an intermediate location between the first and second ferrule ends, wherein the terminal pin groove is positioned adjacent to the first insulator end and the insulator groove, if it exists, is positioned adjacent to the first ferrule end.

7. The feedthrough of claim 6 wherein the first annular groove provided in the terminal pin sidewall is spaced above the first insulator end.

8. The feedthrough of claim 6 wherein the second annular groove provided in the insulator sidewall is spaced above the first ferrule end.

9. The feedthrough of claim 6 wherein the first annular groove provided in the terminal pin sidewall, the second annular groove provided in the insulator sidewall, and the third annular groove provided in the ferrule sidewall are each selected from an annular channel, a sideways facing V-shaped channel and a radiused channel.

10. A feedthrough, which comprises:
   a) an insulator of electrically non-conductive material having a height defined by an insulator sidewall extending to a first insulator end and a second insulator end, wherein the insulator has at least one terminal pin bore extending from the first end to the second end thereof;
   b) a terminal pin received in the terminal pin bore, the terminal pin having a sidewall extending to opposed first and second ends disposed spaced from the respective first and second insulator ends;
   c) a ferrule of an electrically conductive material and comprising a ferrule opening defined by a surrounding sidewall extending to a first ferrule end and a second ferrule end, wherein the insulator is supported in the ferrule opening;
   d) a first braze material hermetically sealing the terminal pin to the insulator and a second braze material hermetically sealing the insulator to the ferrule;
   e) wherein the terminal pin comprises an annular head protruding beyond the terminal pin sidewall as a first braze retaining structure provided in the terminal pin sidewall; and
   f) wherein at least one of the insulator and the ferrule comprise a second braze retaining structure selected from the group consisting of:
      i) the insulator comprises a first annular groove provided in the insulator sidewall at an intermediate location between the first and second insulator ends; and
      ii) a second annular groove provided in the ferrule sidewall at an intermediate location between the first and second ferrule ends, wherein the terminal pin head is positioned adjacent to the first insulator end and the insulator groove, if it exists, is positioned adjacent to the first ferrule end.

11. The feedthrough of claim 10 wherein the terminal pin head is either provided at the first terminal pin end or at an intermediate position between the fist and second terminal pin ends.

12. The feedthrough of claim 10 wherein the terminal pin head is spaced above the first insulator end.

13. The feedthrough of claim 10 wherein the second annular groove provided in the insulator sidewall is spaced above the first ferrule end.

14. The feedthrough of claim 10 wherein the second annular groove provided in the insulator sidewall and the third annular groove provided in the ferrule sidewall are each selected from an annual channel, a sideways facing V-shaped channel and a radiused channel.

* * * * *

UNITED STATES PATENT AND TRADEMARK OFFICE
CERTIFICATE OF CORRECTION

PATENT NO. : 7,145,076 B2 Page 1 of 1
APPLICATION NO. : 11/307434
DATED : December 5, 2006
INVENTOR(S) : Knappen et al.

It is certified that error appears in the above-identified patent and that said Letters Patent is hereby corrected as shown below:

Column 10, line 17: delete "fist" and insert --first--

Signed and Sealed this

Eighth Day of April, 2008

JON W. DUDAS
*Director of the United States Patent and Trademark Office*